United States Patent
Li et al.

(10) Patent No.: US 11,925,503 B2
(45) Date of Patent: Mar. 12, 2024

(54) SHEAR WAVE ELASTICITY IMAGING METHOD AND ULTRASONIC IMAGING DEVICE

(71) Applicant: SHENZHEN MINDRAY BIO-MEDICAL ELECTRONICS CO., LTD., Guangdong (CN)

(72) Inventors: Shuangshuang Li, Shenzhen (CN); Mengling Xu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 478 days.

(21) Appl. No.: 17/087,496

(22) Filed: Nov. 2, 2020

(65) Prior Publication Data

US 2021/0045709 A1    Feb. 18, 2021

Related U.S. Application Data

(63) Continuation of application No. PCT/CN2018/085461, filed on May 3, 2018.

(51) Int. Cl.
*A61B 8/08* (2006.01)
*A61B 8/00* (2006.01)
*A61B 8/14* (2006.01)

(52) U.S. Cl.
CPC .............. *A61B 8/08* (2013.01); *A61B 8/14* (2013.01); *A61B 8/461* (2013.01); *A61B 8/485* (2013.01)

(58) Field of Classification Search
CPC .. A61B 8/08; A61B 8/14; A61B 8/461; A61B 8/485
See application file for complete search history.

(56) References Cited

U.S. PATENT DOCUMENTS

| | | | |
|---|---|---|---|
| 10,251,627 B2 | 4/2019 | Parthasarathy et al. | |
| 2005/0252295 A1 | 11/2005 | Fink et al. | |
| 2013/0058195 A1 | 3/2013 | Cloutier et al. | |
| 2013/0131511 A1 | 5/2013 | Peterson et al. | |
| 2014/0187951 A1 | 7/2014 | Tang et al. | |
| 2015/0119710 A1* | 4/2015 | Kawae ............... | A61B 8/14 600/438 |

(Continued)

FOREIGN PATENT DOCUMENTS

| | | |
|---|---|---|
| CN | 102667522 A | 9/2012 |
| CN | 103908289 A | 7/2014 |

(Continued)

OTHER PUBLICATIONS

PCT International Search Report and the Written Opinion dated Dec. 19, 2018, issued in related International Application No. PCT/CN2018/085461, with partial English translation (10 pages).

(Continued)

*Primary Examiner* — Bo Joseph Peng
(74) *Attorney, Agent, or Firm* — Sheppard Mullin Richter & Hampton LLP

(57) ABSTRACT

Shear wave elasticity imaging methods and ultrasound imaging devices are provided. The method may include: generating a shear wave in a target area of an object being examined; transmitting a first ultrasonic wave to the target area and receiving first echo data; determining an elasticity parameter of the target area according to the first echo data; obtaining a motion parameter of the target area; and displaying the elasticity parameter and the motion parameter.

12 Claims, 3 Drawing Sheets

(56) References Cited

U.S. PATENT DOCUMENTS

2017/0311929 A1    11/2017  Shao et al.
2017/0322308 A1*   11/2017  Loupas ............... G01S 15/8915
2020/0371232 A1    11/2020  Loupas et al.

FOREIGN PATENT DOCUMENTS

| CN | 104622507 A | 5/2015 |
| --- | --- | --- |
| CN | 105212968 A | 1/2016 |
| CN | 105491959 A | 4/2016 |
| CN | 107205724 A | 9/2017 |

OTHER PUBLICATIONS

PCT International Preliminary Report on Patentability dated Nov. 12, 2020, issued in related International Application No. PCT/CN2018/085461, with English translation (13 pages).

First Search dated Mar. 30, 2022, issued in related Chinese Application No. 201880060622.X (2 pages).

* cited by examiner

SHEAR WAVE ELASTICITY IMAGING METHOD AND ULTRASONIC IMAGING DEVICE

CROSS-REFERENCE TO RELATED APPLICATION

This application is a continuation application of International Patent Application No. PCT/CN2018/085461, filed with the China National Intellectual Property Administration (CNIPA) of People's Republic of China on May 3, 2018. The entire content of the above-identified application is incorporated herein by reference.

TECHNICAL FIELD

The present disclosure relates to medical ultrasound imaging, in particular to shear wave elasticity imaging methods and ultrasound imaging devices.

BACKGROUND

Ultrasound elasticity imaging is one of the hotspots of clinical research in recent years. It mainly reflects the elasticity and softness of tissues, and has been increasingly used in the auxiliary detection, discrimination of benign and prognostic evaluation of tissue cancer. According to different imaging principles, ultrasound elasticity imaging technologies are mainly classified into two categories: strain elasticity imaging technology and shear-wave elasticity imaging technology.

In the strain elasticity imaging method, a certain deformation is generated by pressing the tissue with a probe, and then the parameters related to the elasticity of the tissue, such as the strain or the strain rate, may be calculated and imaged, so as to indirectly represent the elastic difference between different tissues. Because the strain parameters are sensitive to pressure, the pressure applied by the probe in this method needs to be as uniform and stable as possible, which puts higher requirements on the operator's technique. In the shear wave elasticity imaging method, the shear wave is generated, and propagates in the tissue, and the propagation parameter (such as the propagation speed) is detected so as to represent the hardness difference between the tissues. Because it no longer relies on the operator's specific pressure on the tissue, this elasticity imaging method has improved stability and repeatability, and the quantitative measurement results make the doctor's diagnosis more convenient and objective.

However, in the shear wave elasticity imaging method, since the vibration amplitude of the shear wave generated in the human tissue is usually small (such as a few um-hundreds of um), and is attenuated very fast, the motion interference during the imaging process will be very likely to cause artifacts, resulting in measurement failure or inaccurate measurement.

SUMMARY

The embodiments of the present disclosure provide shear wave elasticity imaging methods and ultrasound imaging devices, which can provide the parameters or images related to tissue motion while providing the parameters or images related to tissue elasticity, so as to facilitate the user to obtain more accurate elasticity results.

In one embodiment, a shear wave elasticity imaging method is provided, which may include:

transmitting a first ultrasound wave to a target area of an object being examined to track a shear wave propagating in the target area;
receiving an ultrasound echo of the first ultrasound wave returned from the target area to obtain a first echo data;
obtaining an elasticity parameter of the target area according to the first echo data;
obtaining a motion parameter that represents a motion of the target area; and
displaying the elasticity parameter and the motion parameter.

In one embodiment, a shear wave elasticity imaging method is provided, which may include:

obtaining a motion parameter that represents a motion of a target area of an object being examined; and
comparing the motion parameter with a third preset condition, and starting a shear wave elasticity imaging process when the motion parameter meets the third preset condition;
where the shear wave elasticity imaging process may include:
transmitting a first ultrasound wave to the target area of the object being examined to track a shear wave propagating in the target area;
receiving an ultrasound echo of the first ultrasound wave returned from the target area to obtain a first echo data; and
obtaining an elasticity parameter of the target area according to the first echo data.

In one embodiment, a shear wave elasticity imaging method is provided, which may include:

performing a shear wave elasticity imaging process, where the shear wave elasticity imaging process comprises: transmitting a first ultrasound wave to a target area of an object being examined to track a shear wave propagating in the target area; receiving an ultrasound echo of the first ultrasound wave returned from the target area to obtain a first echo data; and obtaining an elasticity parameter of the target area according to the first echo data;
obtaining a motion parameter that represents a motion of the target area; and
comparing the motion parameter with a fourth preset condition, and stopping the shear wave elasticity imaging process when the motion parameter meets the fourth preset condition.

In one embodiment, an ultrasound imaging device is provided, which may include:

an ultrasound probe;
a transmitting/receiving sequence controller configured to excite the ultrasound probe to transmit a first ultrasound wave to a target area of an object being examined to track a shear wave propagating in the target area and receive an ultrasound echo of the first ultrasound wave returned from the target area to obtain a first echo data;
a processor configured to obtain an elasticity parameter of the target area according to the first echo data and obtain a motion parameter that represents a motion of the target area; and
a display configured to display the elasticity parameter and the motion parameter.

In one embodiment, an ultrasound imaging device is provided, which may include:

an ultrasound probe;
a transmitting/receiving sequence controller; and
a processor;

where the processor is configured to obtain a motion parameter that represents a motion of a target area of an object being examined, and compare the motion parameter with a third preset condition and start a shear wave elasticity imaging process when the motion parameter meets the third preset condition;

where the shear wave elasticity imaging process may include:

exciting the ultrasound probe through the transmitting/receiving sequence controller to transmit a first ultrasound wave to the target area of the object being examined to track a shear wave propagating in the target area and receive an ultrasound echo of the first ultrasound wave returned from the target area to obtain a first echo data, and obtaining an elasticity parameter of the target area according to the first echo data.

In one embodiment, an ultrasound imaging device is provided, which may include:

an ultrasound probe;

a transmitting/receiving sequence controller; and a processor;

where, the processor is configured to perform a shear wave elasticity imaging process, where the shear wave elasticity imaging process comprises: exciting the ultrasound probe through the transmitting/receiving sequence controller to transmit a first ultrasound wave to a target area of an object being examined to track a shear wave propagating in the target area and receive an ultrasound echo of the first ultrasound wave returned from the target area to obtain a first echo data, and obtaining an elasticity parameter of the target area according to the first echo data; and the processor is further configured to obtain a motion parameter that represents a motion of the target area, and compare the motion parameter with a fourth preset condition and stop the shear wave elasticity imaging process when the motion parameter meets the fourth preset condition.

In the technical solutions provided by the embodiments of the present disclosure, the ultrasound imaging device may transmit the first ultrasound wave to the target area of the object being examined to track the shear wave propagating in the target area and receive the ultrasound echoes of the first ultrasound wave returned from the target area to obtain the first echo data, and determine the elasticity parameter of the target area according to the first echo data. At the same time, the ultrasound imaging device may obtain the motion parameter representing the movement of the target area, and display the elasticity parameter and the motion parameter. Therefore, during the shear wave elasticity imaging, the user can consider the motion parameter and elasticity parameter. For example, it may be determined that the elasticity parameter obtained when the motion amplitude is small is more reliable, thereby screening out more accurate elasticity result.

DETAILED DESCRIPTION

The technical solutions in the embodiments of the present disclosure will be clearly and completely described below in conjunction with the drawings. Obviously, the described embodiments are only a part, but not all, of the embodiments of the present disclosure.

The terms "first", "second", "third", "fourth", etc. (if any) in the specification, claims and drawings of the present disclosure are used to distinguish similar objects, but not to describe a specific order or sequence. It should be understood that the data used in this way can be interchanged under appropriate circumstances so that the embodiments described herein can be implemented in an order other than the order illustrated or described herein. In addition, the terms "including" and "having" and any variations thereof are intended to mean non-exclusive inclusion. For example, a process, method, system, product or device that includes a series of steps or units is not necessarily limited to the clearly listed steps or units, but may include other steps or units that are not clearly listed or are inherent to the process, method, product or device.

Figure 1:
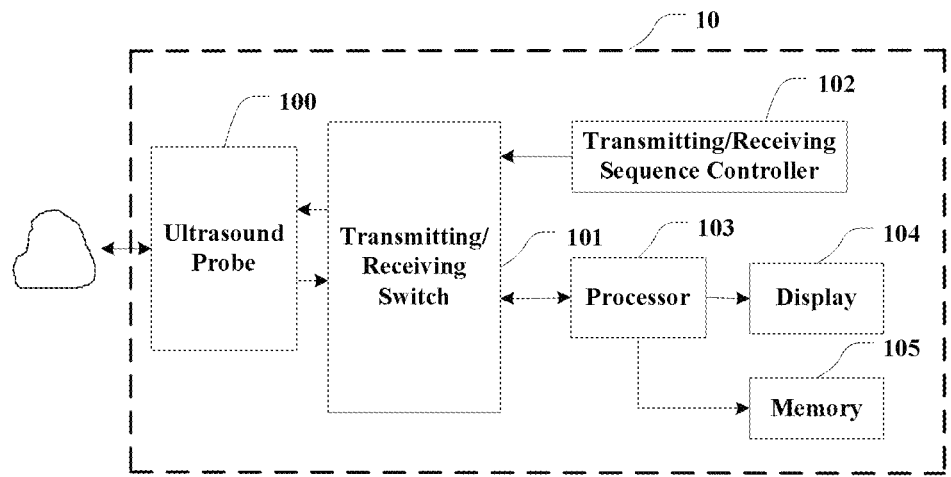
FIG. 1 is a schematic block diagram of the ultrasound imaging device in one embodiment.

FIG. 1 is a schematic block diagram of an ultrasound imaging device 10 in one embodiment of the present disclosure. The ultrasound imaging device 10 may include an ultrasound probe 100, a transmitting/receiving switch 101, a transmitting/receiving sequence controller 102, a processor 103 and a display 104. The transmitting/receiving sequence controller 102 may excite the ultrasound probe 100 to transmit the ultrasound waves to the target area, and may control the ultrasound probe 100 to receive the ultrasound echoes returned from the target area, thereby obtaining the ultrasound echo signal/data. The processor 103 may process the ultrasound echo signal/data to obtain the parameter related to the tissue and the ultrasound image of the target area. The ultrasound images obtained by the processor 103 may be stored in the memory 105, and may be displayed on the display 104.

In the embodiments of the present disclosure, the display 104 of the ultrasound imaging device 10 may be a touch screen, a liquid crystal display, etc., or may be an independent display device such as a liquid crystal display, a television or the like independent of the ultrasound imaging device 10, or may be the display screen on an electronic device such as a mobile phone or a tablet, etc.

In the embodiments of the present disclosure, the memory 105 of the ultrasound imaging device 10 may be a flash memory card, a solid-state memory, a hard disk, or the like.

In the embodiments of the present disclosure, a computer-readable storage medium may also be provided, which may store multiple program instructions. After the multiple program instructions are called and executed by the processor 103, a part or all or any combination of the steps of the shear wave elasticity imaging methods in the embodiments of the present disclosure may be achieved.

In one embodiment, the computer-readable storage medium may be the memory 105, which may be a non-volatile storage medium such as a flash memory card, a solid-state memory, a hard disk, or the like.

In the embodiments of the present disclosure, the processor 103 of the ultrasound imaging device 10 may be implemented by software, hardware, firmware or a combination thereof, and may use circuits, single or multiple application specific integrated circuits (ASIC), single or multiple general-purpose integrated circuits, single or multiple microprocessors, single or multiple programmable logic devices, a combination of the foregoing circuits or devices, or other suitable circuits or devices, such that the processor 103 can perform the steps of the shear wave elasticity imaging methods in the embodiments.

Figure 2:
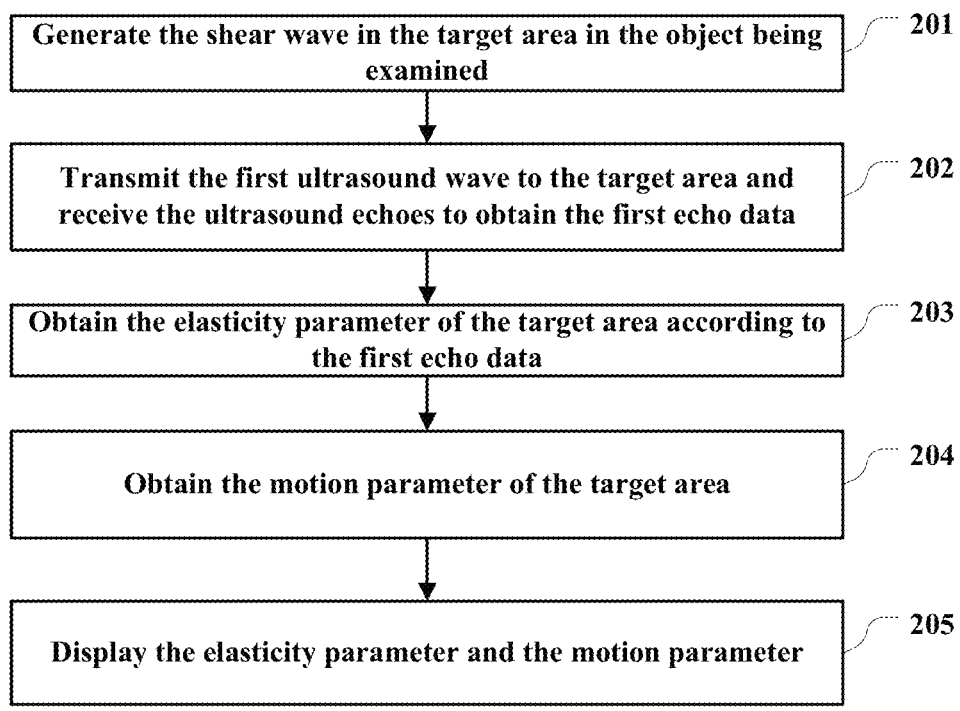
FIG. 2 is a schematic flow chart of the shear wave elasticity imaging method in one embodiment.

The shear wave elasticity imaging methods in the present disclosure will be described in detail below. Referring to FIG. 2, a shear wave elasticity imaging method is provided by one embodiment of the present disclosure, which may be applied to the ultrasound imaging device 10, and be particularly suitable for an ultrasound imaging device 10 that includes a touch screen and can be operated by the inputs inputted through the touch screen. The ultrasound imaging device 10 may use the ultrasound echo data to generate the elasticity images, and may also use the ultrasound echo data to generate the conventional ultrasound B-mode images or the Doppler images. The shear wave elasticity imaging method in one embodiment may include the following steps.

In step 201, a first ultrasound wave may be transmitted to a target area of the object being examined to track a shear wave propagating in the target area.

In this embodiment, the ultrasound imaging device 10 may excite the ultrasound probe 100 through the transmitting/receiving sequence controller 102 to transmit the first ultrasound wave to the target area of the object being examined to track the shear wave propagating in the target area. The target area may be determined according to the needs of the elasticity measurement. For example, the target area may be determined by detection using various applicable imaging modes such as conventional two-dimensional B-mode imaging, conventional elasticity imaging E-mode or the like, or may be selected according to the detection requirements.

In one embodiment, there may be one or multiple target areas. When there are multiple target areas, the longitudinal depths or lateral positions of the multiple target areas may be different.

The shear wave may be generated with the ways described below. In one embodiment, the shear wave may be generated by external vibration. For example, the external vibration may be used to generate the shear wave propagating into the tissue of the target area. Alternatively, the ultrasound pulse acoustic radiation force effect may be used to generate the shear waves in the tissue of the target area. Alternatively, the shear wave may be generated by the physiological movements of the tissue in the object being examined (for example, the heart beat, the blood vessel beat, etc.). Other ways may also be used. These ways will not be described in detail here. In the present disclosure, one commonly used method will be illustrated as an example: ultrasound shear wave elasticity imaging based on acoustic radiation force.

In the ultrasound shear wave elasticity imaging based on acoustic radiation force, the shear waves propagating in the target area may be generated by an ultrasound pulse with a specific waveform, length and frequency transmitted into the tissue by the ultrasound probe 100 excited by the transmitting/receiving sequence controller 102. The ultrasound pulse will produce acoustic radiation force effect inside the tissue, thereby generating the shear wave propagating in the tissue. A series of ultrasound waves may be transmitted to the tissue to track the propagation process of the shear wave in the tissue. It may also be possible to transmit the ultrasound pulse with a specific waveform, length and frequency to the tissue using another ultrasound device, in which the same effect can be achieved based on the acoustic radiation force effect generated by the ultrasound pulse.

In step 202, the ultrasound echoes of the first ultrasound wave returned from the target area may be received to obtain the first echo data.

In this embodiment, the processor 103 may control the ultrasound probe 100 through the transmitting/receiving sequence controller 102 to receive the ultrasound echoes of the first ultrasound wave returned from the target area to obtain the first echo data.

In step 203, the elasticity parameter of the target area may be determined according to the first echo data.

In the present embodiment, the processor 103 may process the first echo data obtained in step 202 to calculate the elasticity parameter of the target area, such as the Young's modulus, the shear modulus, the shear wave propagation velocity or the like. For an isotropic elastomer, the shear wave propagation velocity has the following approximate relationship with the elastic modulus:

$$E=3\rho c^2=3G$$

Where C represents the shear wave propagation velocity, $\rho$ represents the tissue density, E represents the Young's modulus of the tissue, and G represents the shear modulus of the tissue. Normally, the greater the Young's modulus, the harder the tissue. Therefore, the elasticity parameter can represent the hardness of the tissue.

In step 204, the motion parameter that represents the motion of the target area may be obtained.

In this step, the processor 103 may obtain the motion parameter that represents the motion of the target area. The motion parameter may include the respiratory parameter of the human or the displacement of the motion detected by ultrasound waves.

In one embodiment, the processor 103 may detect the breathing motion of the measured object to obtain the respiratory parameter. The respiratory parameter may be the voltage or current obtained by monitoring the breathing through the electrodes, or be the voltage change, the current change or the lung capacity change calculated by the voltage change or the current change.

Figure 3:
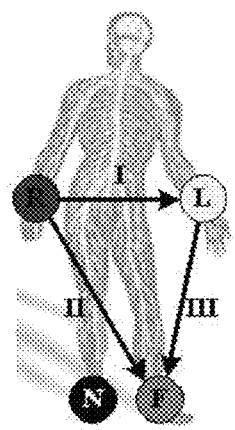
FIG. 3 is a schematic diagram of monitoring the human physiological parameters in one embodiment.

For example, the physiological signal may be obtained from the electrode in a specific part of the human body. After a series of signal processing such as denoising and amplifying, the respiratory parameter that represents the movement of the target area may be obtained. As shown in FIG. 3, three electrodes (electrodes R, L and F in the figure) may be used to obtain the respiratory signals. The electrodes may also be attached to other positions. The positions in FIG. 3 are only for illustration. During the breathing, as the relaxation of the thorax, the electrical impedance of the chest tissue will change. There is a certain correspondence between the change in the electrical impedance of the chest and the change in the lung volume. Therefore, the respiratory motion of the object may be detected to obtain the respiratory parameter by detecting the changes in the electrical impedance of the chest tissue during the breathing through the electrodes.

Further, in one embodiment, the processor 103 may generate a respiratory parameter curve according to the respiratory parameter. Other forms of graphics may also be generated, such as a histogram of respiratory parameters, images or graphics representing the respiratory fluctuations, or the like, which will not be limited here.

Figure 4:
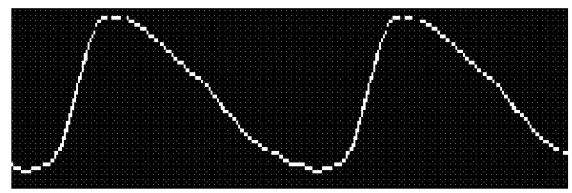
FIG. 4 is a schematic diagram of a breathing curve when the human is breathing normally in one embodiment.
Figure 5:
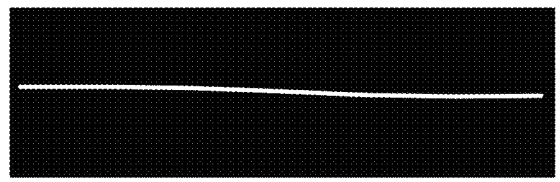
FIG. 5 is a schematic diagram of a breathing curve when the human is holding the breath in one embodiment.

During the elasticity imaging, the display 104 may simultaneously display the respiratory parameter curve and the elasticity parameter. FIG. 4 is a schematic diagram of the respiratory parameter curve when the human is breathing normally, and FIG. 5 is a schematic diagram of the respiratory parameter curve when the human holds the breath. It can be seen that when the human holds the breath, the vibration amplitude of the respiratory parameter curve will decrease. The user can determine that the elasticity parameter obtained when the vibration amplitude is small is reliable, so as to screen out more accurate elasticity result.

In one embodiment, when the elasticity imaging is performed, the ultrasound waves may be used to record the positions of the tissue at different times. By comparing the ultrasound echoes returned at different times, the position difference (i.e. the displacement) of the tissue at different times may be calculated. The parameter related to the displacement may be displayed. The user can determine that the elasticity parameter obtained when the displacement is small is reliable, so as to screen out more accurate elasticity result.

In this embodiment, the ultrasound imaging device 10 may transmit the ultrasound waves for recording the positions of the tissue to the tissue through the ultrasound probe 100 during the elasticity imaging, and receive the ultrasound echoes returned from the tissue to obtain the echo data. This group of ultrasound wave may be the first ultrasound wave used for detecting the shear wave in the shear wave elasticity imaging, or may be ultrasound waves different from the first ultrasound wave.

In one embodiment, the ultrasound waves different from the first ultrasound wave may be used. Specifically, the processor 103 may control the ultrasound probe 100 to transmit the second ultrasound wave to the target area and receive the ultrasound echoes of the second ultrasound wave returned from the target area to obtain the second echo data, and obtain at least two frames of ultrasound images of the target area according to the second echo data, so as to determine the displacement of the tissue in the target area according to the at least two frames of ultrasound images.

In one embodiment, the first ultrasound wave used for detecting the shear wave in the shear wave elasticity imaging described above may also be used to detect the displacement of the target area. Specifically, the processor 103 may obtain at least two frames of ultrasound images of the target area according to the first echo data, and determine the displacement of the tissue in the target area according to the at least two frames of ultrasound images.

In one embodiment, the processor 103 may generate the displacement curve according to the displacement of the target area. It may also be possible to generate other forms of graphics, such as a displacement amplitude distribution map, a displacement vector distribution map, an image or graph representing the displacement change, or the like, which will not be limited herein.

Figure 6:
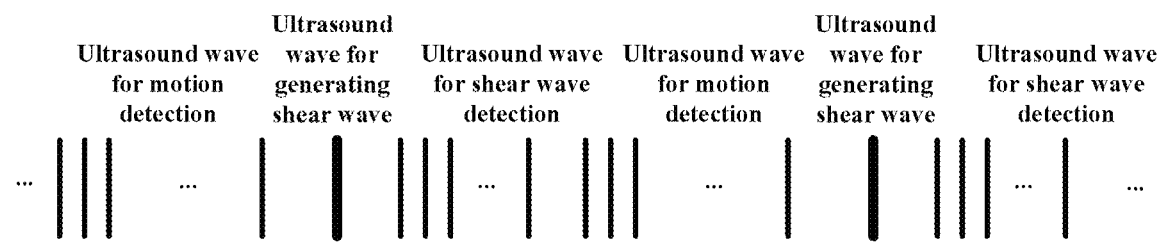
FIG. 6 is a schematic diagram of a sequence for detecting the tissue motion in one embodiment.

Detecting the displacement using the ultrasound wave different from the first ultrasound wave will be illustrated as an example. FIG. 6 shows a schematic diagram of the ultrasound waves for detecting the tissue motion. In FIG. 6, the ultrasound waves for detecting the displacement of the tissue and the ultrasound waves of the first ultrasound wave for detecting the shear wave in the shear wave elasticity imaging may be transmitted and received independently.

In one embodiment, when detecting the displacement of the tissue using the ultrasound waves, the displacement detection may be performed solely for the tissue at a certain local position. Alternatively, the displacement of the tissue in a large area as a whole may be detected. Alternatively, the displacements of the tissue at each local position within a large area may be detected respectively.

In one embodiment, determining the displacement of the tissue in the target area according to the at least two frames of ultrasound images may include:

determining an area to be matched from a first frame of ultrasound image of the at least two frames of ultrasound images;

determining a matching area that matches the area to be matched from a second frame of ultrasound image of the at least two frames of ultrasound images; and determining the displacement according to the area to be matched and the matching area.

Figure 7:
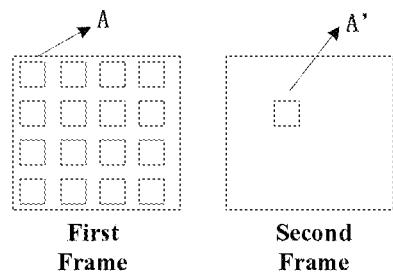
FIG. 7 is a schematic diagram of the displacement detection method in one embodiment.

Regarding the method for detecting the displacement of the tissue in the target area according to the at least two frames of ultrasound images, reference may be made to the following description. As shown in FIG. 7, taking two frames of ultrasound images as an example, the figure shows the echo signals corresponding to the two frames of ultrasound images (the first frame and the second frame in the figure). The area A to be matched may be selected from the first frame. Thereafter, the searching may be performed in the second frame, and the position with the maximum correlation with the area A may be determined as the matching area A' that matches the area A to be matched. The position difference between A and A' may be the displacement. In this way, the amplitude and direction of the movement of the area A to be matched may be calculated.

After the displacement between the area to be matched and the matching area is obtained, it may be displayed in various ways. For example, the average displacement amplitude of the tissue in the region of interest at different times may be obtained and drawn into a curve that changes with time to obtain a displacement curve. For example, the displacement information of the tissue in the region of interest at different times may be calculated and drawn into a displacement amplitude distribution map changing with time. For example, the displacement information of the tissue in the region of interest at different times may be calculated and drawn into a displacement vector distribution map changing with time. The displacement vector may be represented by an arrow with a certain length, where the arrow direction represents the displacement direction and the arrow length represents the displacement amplitude. For example, the displacement information in the region of interest at different times may be calculated and displayed with different colors according to their amplitudes. For example, the displacements whose amplitudes are within a certain range may be displayed with red, the displacements whose amplitudes are within another certain range may be displayed in green, and so on.

In step 205, the elasticity parameter and the motion parameter may be displayed.

In this step, the elasticity parameter and the motion parameter obtained by the processor 103 may be displayed on the display 104 simultaneously or separately.

The processor 103 may generate an elasticity image according to the elasticity parameter, or generate a motion image according to the motion parameter, and control the display 104 to display the elasticity image and the motion image.

In the solutions above, the ultrasound imaging device 10 may control the ultrasound probe 100 to transmit the first ultrasound wave to the target area of the object being examined to track the shear wave propagating in the target area and receive the ultrasound echoes of the first ultrasound wave returned from the target area to obtain the first echo data, and determine the elasticity parameter of the target area according to the first echo data. Meanwhile, the ultrasound imaging device 10 may obtain the motion parameter representing the movement of the target area through the processor 103, and display the elasticity parameter and the motion parameter. Therefore, when performing the shear wave elasticity imaging, the user can consider the motion parameter and the elasticity parameter. For example, it may be determined that the elasticity parameter obtained when the motion amplitude is small is more reliable, so as to screen out more accurate elasticity result.

In one embodiment, the processor may also determine the reliability of the elasticity parameter according to the obtained motion parameter. Further, the ultrasound imaging device 10 may also provide corresponding prompts according to the motion threshold parameter preset by the device or set by the user.

In one embodiment, the motion parameter may be compared with a first preset condition. When the motion parameter meets the first preset condition, it may be determined that the elasticity parameter or elasticity image obtained when the motion parameter satisfies the first preset condition has a high reliability.

In one embodiment, the motion parameter may be compared with a second preset condition, and when the motion parameter meets the second preset condition, it may be determined that the elasticity parameter or elasticity image obtained when the motion parameter meets the second preset condition has a low reliability.

The first preset condition may be set according to the type of the motion parameter. Taking the motion parameter being the respiratory parameter as an example, the respiratory parameter may be the voltage or current obtained when monitoring the breathing of the human through the electrodes, or may be the voltage change, the current change or the lung capacity change calculated by the voltage change or the current change. In the case that the motion parameter is the voltage, the first preset condition may be a first preset value. When the voltage is less than the first preset value, it may be determined that the elasticity parameter or elasticity image obtained at this time has high reliability. Similarly, the second preset condition may be a second preset value, and when the voltage is greater than the second preset value, it may be determined that the elasticity parameter or elasticity image obtained at this time has low reliability. In the case that the motion parameter is the current, the first preset condition may be a third preset value. When the current is greater than the third preset value, it may be determined that the elasticity parameter or elasticity image obtained at this time has high reliability. Similarly, the second condition may be a fourth preset value, and when the current is less than the fourth preset value, it may be determined that the elasticity parameter or elasticity image obtained at this time has low reliability. In the case that the motion parameter is the displacement, the first preset condition may be a fifth preset value. When the displacement is less than the fifth preset value, it may be determined that the elasticity parameter or elasticity image obtained at this time has high reliability. Similarly, the second preset condition may be a sixth preset value, and when the displacement is greater than the sixth preset value, it may be determined that the elasticity parameter or elasticity image obtained at this time has low reliability.

For other forms of motion parameters, the preset conditions may be set with reference to the solutions above, which will not be listed here.

Further, after determining the reliability of the obtained elasticity parameter or elasticity image according to the motion parameter, the ultrasound imaging device 10 may output a corresponding prompt so as to prompt the user that the elasticity parameter or elasticity image obtained when the motion parameter meets the first preset condition has high reliability or the elasticity parameter or elasticity image obtained when the motion parameter meets the second preset condition has low reliability. The prompt may be a voice, a text, a dialog box, a graphics, a highlighting, an area where the elasticity parameter/elasticity image is displayed with a specific color, or the like, which will not be limited herein.

Figure 8:
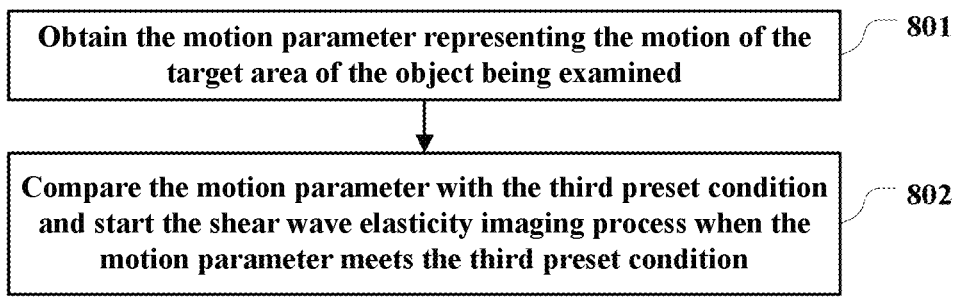
FIG. 8 is another schematic flow chart of the shear wave elasticity imaging method in one embodiment.

In one embodiment, a shear wave elasticity imaging method may also be provided that is suitable for the ultrasound imaging device 10. Referring to FIG. 8, the method may include the following steps.

In step 801, the motion parameter that represents the motion of the target area of the object being examined may be obtained.

Regarding this step, reference may be made to the description of step 204 in the foregoing embodiment, which will not be described again here.

In step 802, the motion parameter may be compared with a third preset condition, and a shear wave elasticity imaging may be started when the motion parameter meets the third preset condition.

The processor 103 may start or stop the shear wave elasticity imaging according to the obtained motion parameter.

In one embodiment, the processor 103 may compare the motion parameter with a fourth preset condition, and stop the shear wave elasticity imaging when the motion parameter meets the fourth preset condition.

It should be noted that the third preset condition may be set according to the type of the motion parameter. Taking the motion parameter being the respiratory parameter as an example, the respiratory parameter may be the voltage or current obtained when monitoring the breathing of the human through the electrodes, or may be the voltage change, the current change or the lung capacity change calculated by the voltage change or the current change. In the case that the motion parameter is the voltage, the third preset condition may be a seventh preset value, and when the voltage is less than the seventh preset value, it may be determined to start the shear wave elasticity imaging. Similarly, the fourth preset condition may be an eighth preset value, and when the voltage is greater than the eighth preset value, it may be determined to stop the shear wave elasticity imaging. In the case that the motion parameter is a current, the third preset condition may be a ninth preset value, and when the current is greater than the ninth preset value, it may be determined to start the shear wave elasticity imaging. Similarly, the fourth preset condition may be a tenth preset value, and when the current is less than the tenth preset value, it may be determined to stop the shear wave elasticity imaging. In the case that the motion parameter is the displacement, the third preset condition may be a eleventh preset value, and when the displacement is less than the eleventh preset value, it may be determined to start the shear wave elasticity imaging. Similarly, the fourth preset condition may be a twelfth preset value, and when the displacement is greater than the twelfth preset value, it may be determined to stop the shear wave elasticity imaging.

For other forms of motion parameters, the preset conditions may be set with reference to the solutions above, which will not be listed herein.

The shear wave elasticity imaging may include:
transmitting the first ultrasound wave to the target area of the object being examined to track the shear wave propagating in the target area;
receiving the ultrasound echoes of the first ultrasound wave returned from the target area to obtain the first echo data; and
obtaining the elasticity parameter of the target area according to the first echo data.

Regarding the shear wave elasticity imaging, reference may be made to steps 201 to 203 in the foregoing embodiment, which will not be described again here.

Figure 9:
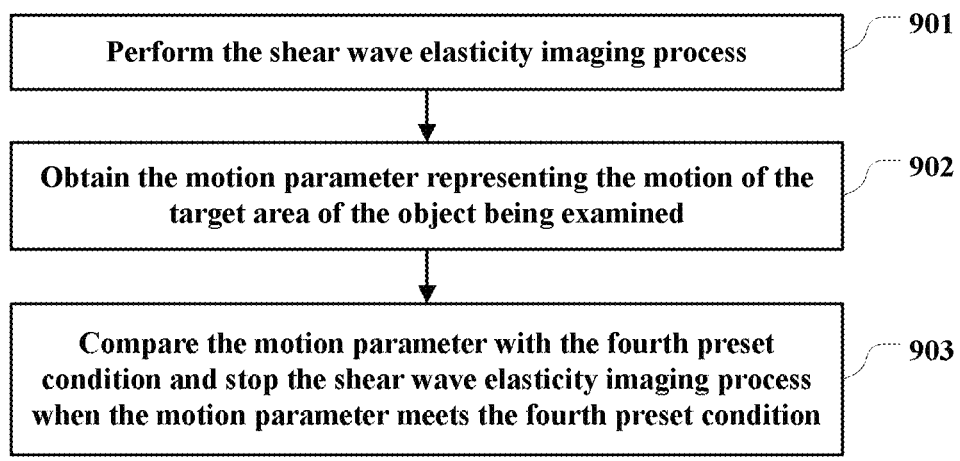
FIG. 9 is another schematic flow chart of the shear wave elasticity imaging method in one embodiment.

In one embodiment, a shear wave elasticity imaging method may be provided, which may be suitable for the ultrasound imaging device 10. Referring to FIG. 9, the method may include the following steps.

In step 901, the shear wave elasticity imaging may be performed.

The shear wave elasticity imaging may include: transmitting the first ultrasound wave to the target area of the object being examined to track the shear wave propagating in the target area; receiving the ultrasound echoes of the first ultrasound wave returned from the target area to obtain the first echo data; and obtaining the elasticity parameter of the target area according to the first echo data.

This step may be understood with reference to steps 201 to 203 in the foregoing embodiment, and will not be described in detail here.

In step 902, the motion parameter that represents the motion of the target area of the object being examined may be obtained.

This step may be understood with reference to the description of step 204 in the foregoing embodiment, and will not be described in detail here.

In step 903, the motion parameter may be compared with the fourth preset condition, and when the motion parameter meets the fourth preset condition, the shear wave elasticity imaging may be stopped.

The processor 103 may compare the motion parameter with the fourth preset condition, and stop the shear wave elasticity imaging process when the motion parameter meets the fourth preset condition. In one embodiment, the processor 103 may compare the motion parameter with the fourth preset condition, and, when the motion parameter meets the fourth preset condition, the processor 103 may stop the shear wave elasticity imaging process after a delay of a period of time (for example, a delay of 100 ms, 1 s, etc.).

It should be noted that the fourth preset condition may be set according to the type of the motion parameter. Taking the motion parameter being the respiratory parameter as an example, the respiratory parameter may be the voltage or current obtained when monitoring the breathing of the human through the electrodes, or may be the voltage change, the current change or the lung capacity change calculated by the voltage change or the current change. In the case that the motion parameter is the voltage, the fourth preset condition may be a eighth preset value, and when the voltage is great than the eighth preset value, it may be determined to stop the shear wave elasticity imaging. In the case that the motion parameter is a current, the fourth preset condition may be a tenth preset value, and when the current is less than the tenth preset value, it may be determined to stop the shear wave elasticity imaging. In the case that the motion parameter is the displacement, the fourth preset condition may be a twelfth preset value, and when the displacement is greater than the twelfth preset value, it may be determined to stop the shear wave elasticity imaging.

For other forms of motion parameters, the preset conditions may be set with reference to the solutions above, which will not be listed herein.

The embodiments above may be implemented entirely or partly by software, hardware, firmware or any combination thereof. When implemented by software, they can be implemented entirely or partly in the form of a computer program product.

The computer program product may include one or more computer instructions. When the computer instructions are loaded and executed in the computer, the processes or functions described in the embodiments of the present disclosure may be generated in whole or in part. The computer may be a general-purpose computer, a special-purpose computer, a computer network, or other programmable devices. The computer instructions may be stored in a computer-readable storage medium, or be transmitted from one computer-readable storage medium to another computer-readable storage medium. For example, the computer instructions may be transmitted from a website, computer, server or data center to another website, computer, server or data center via wired (such as coaxial cable, optical fiber, Digital Subscriber Line (DSL)) or wireless (such as infrared, wireless, microwave, etc.) connection. The computer-readable storage medium may be any available medium that can be used for storing by a computer or a data storage device such as an integrated server or data center which include one or more available media. The available medium may be a magnetic medium (such as a floppy disk, a hard disk, a magnetic tape), an optical medium (such as a DVD), a semiconductor medium (such as a solid state hard disk (SSD) or the like.

Those skilled in the art can clearly understand that, regarding the specific working process of the system, device and unit described above, reference may be made to the corresponding processes in the methods described above, which, for the convenience and conciseness of the description, will not be repeated here.

It should be understood that in the embodiments of the present disclosure the disclosed systems, devices and methods may be implemented in other ways. For example, the devices described above are only illustrative. For example, the division of the units is only a logical function division, and there may be other divisions in actual implementation. For example, multiple units or components may be combined or be integrated into another system. Some features may be ignored or not implemented. In addition, the displayed or discussed mutual coupling or direct coupling or communication connection may be indirect coupling or communication connection through some interfaces, devices or units, and may be in electrical, mechanical or other forms.

The units described as separate components may or may not be physically separated. The components displayed as units may or may not be physical units, that is, they may be located in one place, or they may be distributed on multiple network units. Some or all of the units may be selected according to actual needs to achieve the objectives of the solutions of the embodiments.

In addition, the functional units in the embodiments of the present disclosure may be integrated into one unit. Alternatively, the units may exist alone physically. Alternatively, two or more units may be integrated into one unit. The integrated unit may be implemented in the form of hardware or software functional unit.

In the case that the integrated unit is implemented in the form of a software functional unit and sold or used as an independent product, it may be stored in a computer readable storage medium. Based on this understanding, the essential part or the part that contributes to the existing technology or all or part of the technical solutions of the present disclosure may be embodied in the form of a software product. The software product may be stored in a storage medium, and may include multiple instructions which may be used to make a computer device (which may be a personal computer, a server, or a network device, etc.) to execute all or part of the steps of the method described in the embodiments of the present disclosure. The storage media may include a U disk, a mobile hard disk, a read-only memory (ROM), a random access memory (RAM), a magnetic disk, an optical disk or other media that can store program code.

The embodiments above are only used to illustrate, but not limit, the technical solutions of the present disclosure. Although the present disclosure has been described in detail with reference to the embodiments above, those of ordinary skill in the art should understand that the technical solutions in the embodiments may be modified or some of the technical features may be equivalently replaced. These modifications or replacements will not cause the essence of the corresponding technical solutions to deviate from the spirit and scope of the technical solutions in the embodiments of the present disclosure.

The invention claimed is:

1. A shear wave elasticity imaging method, comprising:
   transmitting a first ultrasound wave to a target area of an object being examined to track a shear wave propagating in the target area;
   receiving an ultrasound echo of the first ultrasound wave returned from the target area to obtain a first echo data;
   obtaining an elasticity parameter of the target area according to the first echo data;
   obtaining a motion parameter that represents a motion of the target area, wherein obtaining the motion parameter comprising:
      obtaining at least two frames of ultrasound images of the target area according to the first echo data; and
      obtaining a displacement of a tissue in the target area according to the at least two frames of ultrasound images; and
   displaying the elasticity parameter and the motion parameter.

2. The method of claim 1, further comprising:
   generating an elasticity image according to the elasticity parameter; and
   generating a motion image according to the motion parameter;
   wherein displaying the elasticity parameter and the motion parameter comprises:
   displaying the elasticity image and the motion image.

3. The method of claim 1, wherein obtaining the motion parameter that represents the motion of the target area comprises:
   detecting a respiratory motion of the object being examined to obtain a respiratory parameter.

4. The method of claim 3, further comprising:
   generating a respiratory parameter curve according to the respiratory parameter.

5. The method of claim 1, further comprising:
   generating a displacement curve according to the displacement of the tissue in the target area.

6. The method of claim 1, wherein obtaining the displacement of the tissue in the target area according to the at least two frames of ultrasound images comprises:
   determining an area to be matched from a first frame of ultrasound image of the at least two frames of ultrasound images;
   determining a matching area that matches the area to be matched from a second frame of ultrasound image of the at least two frames of ultrasound images; and
   obtaining the displacement according to the area to be matched and the matching area.

7. The method of claim 1, before transmitting the first ultrasound wave to the target area of the object being examined, further comprising:
   generating the shear wave that propagates in the target area.

8. The method of claim 1, further comprising:
   determining a reliability of the elasticity parameter according to the motion parameter.

9. The method of claim 8, wherein determining the reliability of the elasticity parameter according to the motion parameter comprises:
   comparing the motion parameter with a first preset condition, and when the motion parameter meets the first preset condition, determining that the elasticity parameter or elasticity image obtained when the motion parameter meets the first preset condition has high reliability.

10. The method of claim 9, further comprising:
    outputting a first prompt, wherein the first prompt is used for prompting that the elasticity parameter or elasticity image obtained when the motion parameter meets the first preset condition has high reliability.

11. The method of claim 8, wherein determining the reliability of the elasticity parameter according to the motion parameter comprises:
    comparing the motion parameter with a second preset condition, and when the motion parameter meets the second preset condition, determining that the elasticity parameter or elasticity image obtained when the motion parameter meets the second preset condition has low reliability.

12. The method of claim 11, further comprising:
    outputting a second prompt, wherein the second prompt is used for prompting that the elasticity parameter or elasticity image obtained when the motion parameter meets the second preset condition has low reliability.

* * * * *